(12) United States Patent
Wu et al.

(10) Patent No.: US 11,546,572 B2
(45) Date of Patent: Jan. 3, 2023

(54) NONINVASIVE THREE-DIMENSIONAL FLUORESCENCE MICROSCOPY FOR SKIN DISEASE DETECTION

(71) Applicant: Rowan University, Glassboro, NJ (US)

(72) Inventors: Ben Wu, Glassboro, NJ (US); Ying Tang, Glassboro, NJ (US); Xiao Hu, Glassboro, NJ (US)

(73) Assignee: Rowan University, Glassboro, NJ (US)

( * ) Notice: Subject to any disclaimer, the term of this patent is extended or adjusted under 35 U.S.C. 154(b) by 0 days.

(21) Appl. No.: 17/051,597

(22) PCT Filed: May 21, 2019

(86) PCT No.: PCT/US2019/033335
§ 371 (c)(1),
(2) Date: Oct. 29, 2020

(87) PCT Pub. No.: WO2019/226664
PCT Pub. Date: Nov. 28, 2019

(65) Prior Publication Data
US 2021/0243424 A1 Aug. 5, 2021

Related U.S. Application Data

(60) Provisional application No. 62/674,213, filed on May 21, 2018.

(51) Int. Cl.
*H04N 13/254* (2018.01)
*G06T 7/521* (2017.01)
(Continued)

(52) U.S. Cl.
CPC ......... *H04N 13/254* (2018.05); *G06T 7/521* (2017.01); *H04N 5/372* (2013.01);
(Continued)

(58) Field of Classification Search
CPC ................. H04N 13/254; H04N 5/372; H04N 2013/0081; G06T 7/521;
(Continued)

(56) References Cited

U.S. PATENT DOCUMENTS

| 5,061,049 A | 10/1991 | Hornbeck | |
| 5,159,361 A * | 10/1992 | Cambier | A61B 3/107 351/212 |

(Continued)

FOREIGN PATENT DOCUMENTS

| EP | 2730209 A1 | 5/2014 | |
| WO | 0239873 A2 | 5/2002 | |
| WO | WO-0239873 A2 * | 5/2002 | ......... A61B 5/14553 |

OTHER PUBLICATIONS

International Search Report and Written Opinion, International Patent Application No. PCT/US2019/033335, dated Jul. 18, 2019.
(Continued)

*Primary Examiner* — Sath V Perungavoor
*Assistant Examiner* — Kristin Dobbs
(74) *Attorney, Agent, or Firm* — Saul Ewing LLP; Domingos J. Silva

(57) ABSTRACT

Methods and systems for digitally reconstructing a patient tissue sample are described herein. In one embodiment, the method may include projecting a first structured light pattern onto the patient tissue sample, receiving a first reflection of the first structured light pattern from the patient tissue sample, and reconstructing the patient tissue sample based on the first reflection and the projected first structured light pattern. In another embodiment, the system may include a projector adapted or configured to project the first structured light onto the patient tissue sample, a charge-coupled device (CCD) adapted or configured to receive the first reflection from the patient tissue sample, and a reconstruction device
(Continued)

adapted or configured to reconstruct the patient tissue sample based on the first reflection and the projected first structured light pattern.

10 Claims, 7 Drawing Sheets

(51) Int. Cl.
 *H04N 5/372* (2011.01)
 *H04N 13/00* (2018.01)
(52) U.S. Cl.
 CPC .............. *G06T 2207/10056* (2013.01); *G06T 2207/10064* (2013.01); *G06T 2207/30024* (2013.01); *G06T 2207/30088* (2013.01); *H04N 2013/0081* (2013.01)
(58) Field of Classification Search
 CPC . G06T 2207/10056; G06T 2207/10064; G06T 2207/30024; G06T 2207/30088
 USPC .......................................................... 348/46
 See application file for complete search history.

(56) References Cited

U.S. PATENT DOCUMENTS

| | | | |
|---|---|---|---|
| 9,626,568 B2 | 4/2017 | Tang et al. | |
| 2015/0141847 A1* | 5/2015 | Sarvazyan | A61B 5/0075 600/478 |
| 2017/0336326 A1* | 11/2017 | Sirat | G01N 21/636 |
| 2019/0206050 A1 | 7/2019 | Yates et al. | |

OTHER PUBLICATIONS

Wikipedia, "Digital micromirror device", https://en.wikipedia.org/wiki/Digital_micromirror_device, downloaded May 17, 2019, 2 pages.

\* cited by examiner

NONINVASIVE THREE-DIMENSIONAL FLUORESCENCE MICROSCOPY FOR SKIN DISEASE DETECTION

CROSS-REFERENCE TO RELATED APPLICATION(S)

This application is a national phase application under 35 U.S.C. 371 of International Application No. PCT/US2019/033335, filed May 21, 2019, which claims priority to U.S. Provisional Patent Application Ser. No. 62/674,213, filed May 21, 2018. This application is also related to U.S. Pat. No. 9,626,568 filed on Nov. 26, 2013. The entire content of these applications are hereby incorporated by reference herein.

BACKGROUND OF THE INVENTION

Conventional skin disease detection techniques avoid using fluorescence microscopy until the very late stage of the disease. Existing 3D fluorescence microscopy methods require sample preparation and tissue cut from human skin, which damages the disease area. Furthermore, current 3D fluorescence microscopy methods, including confocal microscopy, and optical coherence tomography (OCT), are based on scanning techniques, which require skin exposure to laser radiation for a period of time in the orders of seconds to minutes. Even though researchers have been continuously improving those methods, the long exposure time to laser results in few practical applications for live measurement of skin diseases.

SUMMARY

One aspect of the invention provides for a method of digitally reconstructing a patient tissue sample. In one embodiment, the method includes projecting a first structured light pattern onto the patient tissue sample, receiving a first reflection of the first structured light pattern from the patient tissue sample, and reconstructing the patient tissue sample based on the first reflection and the projected first structured light pattern.

This aspect of the invention can include a variety of embodiments.

In one embodiment, the method further includes projecting a second structured light pattern onto the patient tissue sample subsequent to the projected first structured light pattern, receiving a second reflection of the second reflection of the second structured light pattern from the patient tissue sample, and where reconstructing the patient tissue sample is further based on the second reflection and the projected second structured light pattern. In some cases, the projected second structured light pattern is projected onto the patient tissue sample at a predetermined angle relative to the projected first structured light pattern, where reconstructing the patient tissue sample is further based on the predetermined angle.

In one embodiment, the method further includes comparing the first reflection and the first structured light pattern, and determining a depth of a portion of the patient tissue sample based on the comparing.

In one embodiment, first light pattern is projected onto the patient tissue sample for less than 5 ms. In one embodiment, the patient tissue sample includes an uncut and untreated tissue sample. In one embodiment, a surface area for the patient tissue sample is less than 1 cm². In one embodiment, the projected first structured light pattern includes a set of horizontal lines, a set of vertical lines, or a combination thereof. In some cases, a spacing between two adjacent vertical lines or two adjacent horizontal lines includes 0.05 mm.

In one embodiment, the method further includes displaying the reconstructed patient tissue sample on a graphical user interface.

One aspect of the invention provides for a system for digitally reconstructing a patient tissue sample according to the methods described herein. In one embodiment, the system includes a projector adapted or configured to project the first structured light onto the patient tissue sample, a charge-coupled device (CCD) adapted or configured to receive the first reflection from the patient tissue sample, and a reconstruction device adapted or configured to reconstruct the patient tissue sample based on the first reflection and the projected first structured light pattern.

This aspect of the invention can include a variety of embodiments.

In one embodiment, the system can further include a tunable filter positioned between the projector and the patient tissue sample, the tunable filter adapted or configured to reduce a surrounding light intensity being received by the patient tissue sample.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

Figure 1:
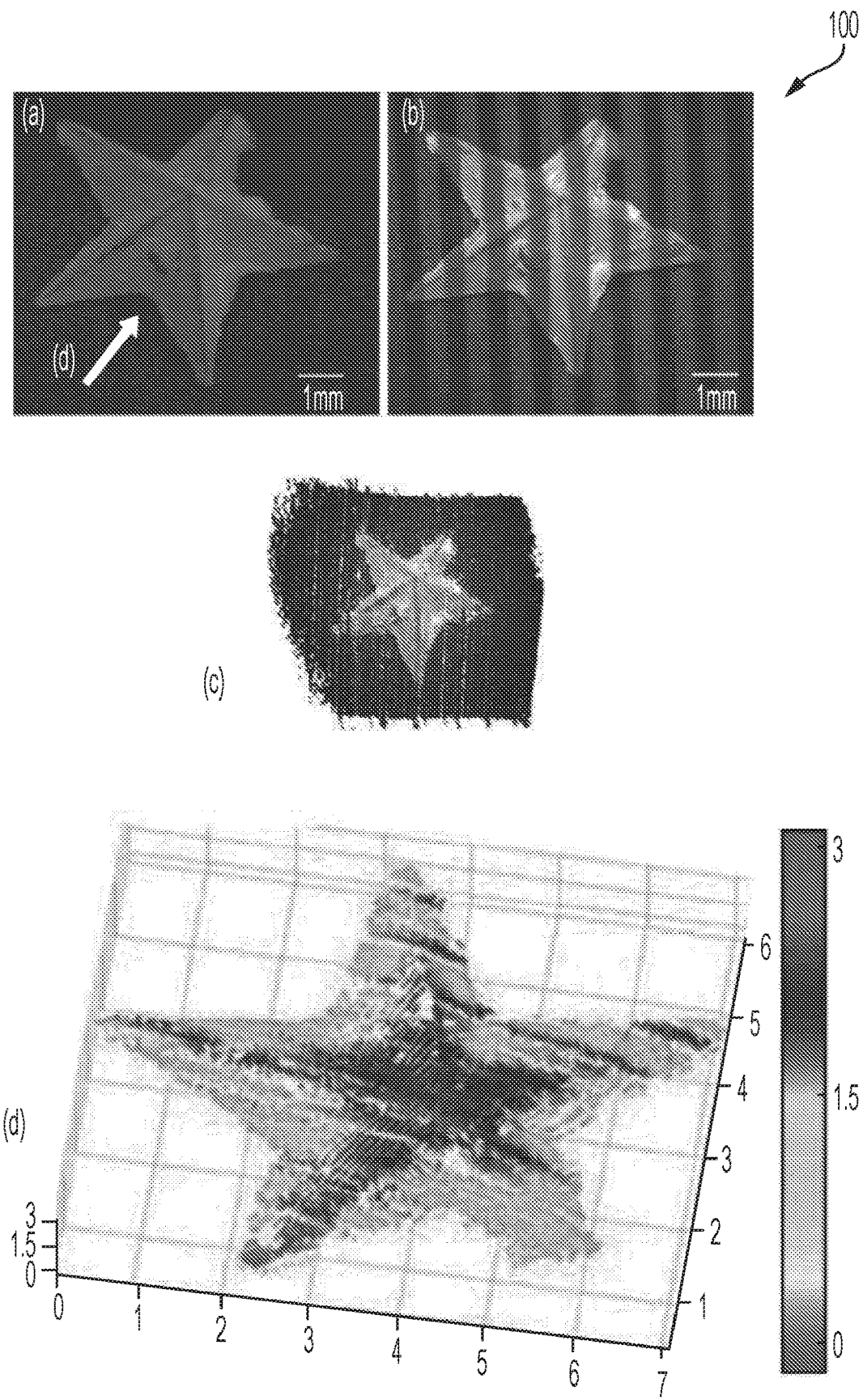
FIG. 1 depicts a subject for 3-D fluorescence microscopy according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

In certain aspects, the invention provides a system and associated method for noninvasive 3-D fluorescence microscopy.

The claimed system and method aims for early detection of skin diseases because it is noninvasive and can be applied directly to live human skin. It captures the 3D fluorescence images in a few milliseconds, which is at least 3 orders of magnitude faster than the existing technologies. The short imaging time enables the test on a live human body without sample preparation, so early detection can be performed to the skin disease.

A feature of this technology includes the short imaging time, which enables live imaging of human skin for two reasons. First, it is impractical to hold the skin of a live body stable at the focus plane of a microscopic imaging system for several seconds. The existing methods require seconds to minutes to obtain an image, while the proposed system can capture images in a few milliseconds when the skin is moving around the focus plane. Second, as a fluorescence imaging method, the short imaging time corresponds to less exposure to the laser, so the damage to the human skin is at least three orders of magnitude smaller than the existing methods.

Further, dermatologists can use this method and system to perform noninvasive tests for early detection of skin diseases. According to a recent report by the American Academy of Dermatology, more than 85 million people in the U.S. are affected by skin diseases, and the direct cost of treating skin diseases in the United States is about $75 billion per year. The cure rate of skin diseases drops exponentially with the length of time before the diseases are detected. The claimed invention can detect the skin disease at an early stage and will significantly benefit the more than 85 million people who either are currently suffering from or might potentially suffer from skin diseases.

Light Input

Figure 2:
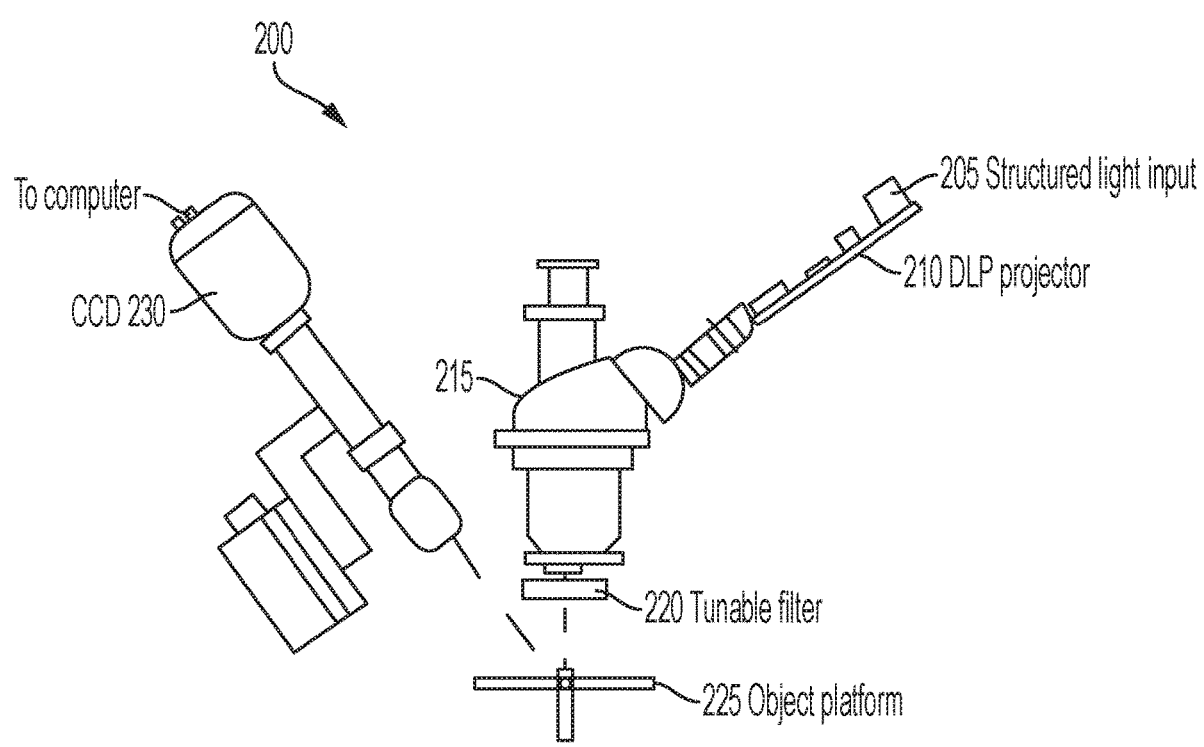
FIGS. 2-4 depict systems for 3-D fluorescence microscopy according to embodiments of the invention.
Figure 3:
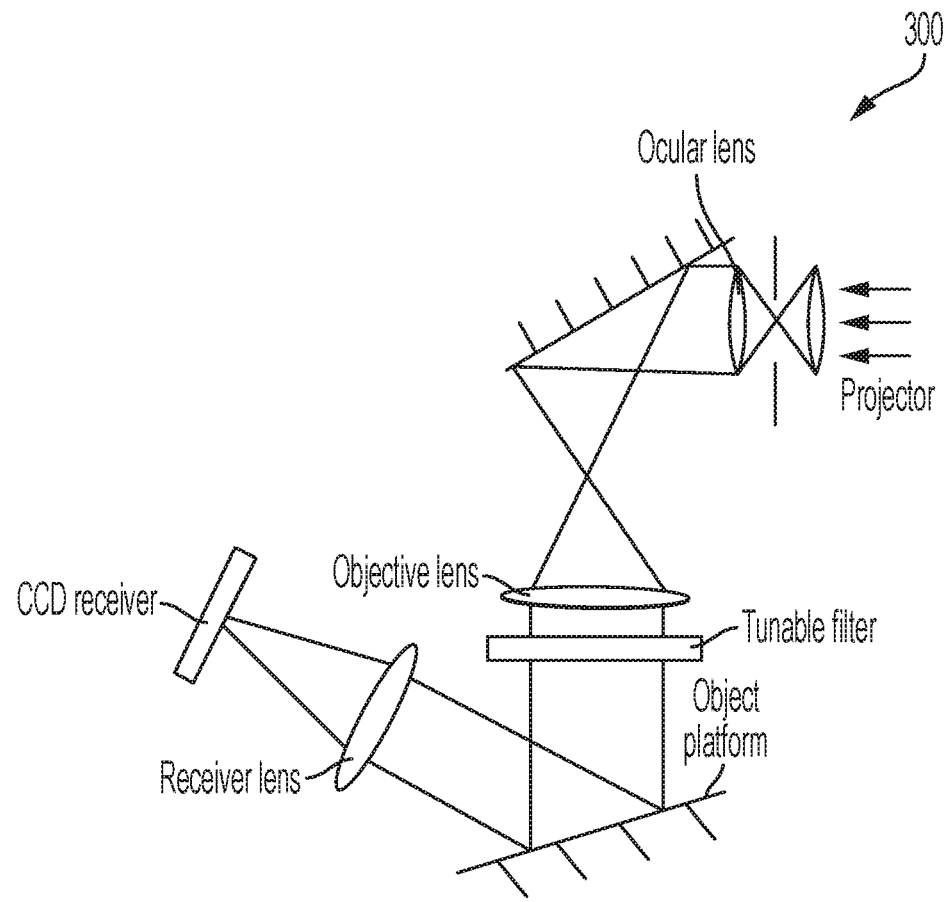
Figure 4:
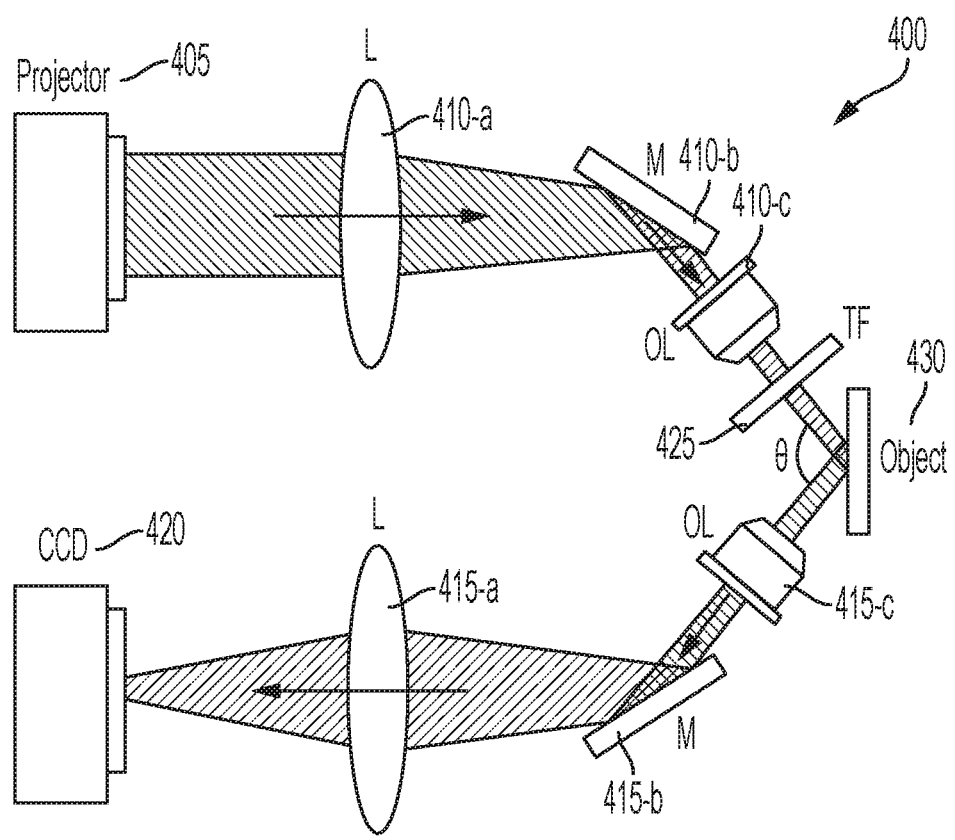

FIGS. 2-4 provide exemplary systems 200, 300, and 400 for 3-D fluorescence microscopy according to embodiments of the claimed invention. System 200 includes light input 205. The light input emits structured light through the system 200 with a specified resolution (e.g., 608×864 pixels). The structured light can include a specified pattern. For example, the light can be transmitted in a bar pattern, where the light is transmitted in individual bars spaced apart (e.g., a set of vertical bars with spacing, a set of horizontal bars with spacing, etc.). In another example, the light can be transmitted in a grid pattern. For example, the light input 205 can transmit light with a set of lattices (e.g., in a grid pattern). In some cases, the light input 205 can include uniform light (e.g., uniform light wavelengths) throughout the pattern. In other cases, the light input 205 can include varying light for different portions of the pattern. Further, while laser light is an exemplary type of light source for the light input 205 (e.g., due to its ability to coherently emit light and produce finely granular patterns), other types of light emission that are known in the art can be used as well.

Light Projector

The light projector 210 receives the emitted light input 205 and projects the structured light onto the tissue sample. In some cases, the light projector 210 can be a set of lenses configured to project the light input 205. In some cases, the light projector can be a digital light projector (DLP). The light projector 210 projects the structured light at a specified ratio (e.g., 16:9). Depending upon the predetermined pattern chosen for the light input 205, the projector 210 can project the structured light with the predetermined light pattern. Thus, the tissue sample receives the projected version of the light pattern from the light input 205. Further, the predetermined pattern can include spacing between received light (e.g., the vertical bars, horizontal bars, etc.), and thus the tissue sample may receive light patterns with predetermined spacing between received light (e.g., between 50 μm to 10 mm distance between patterns).

In addition, the light projector can alter the light pattern transmitted to the sample in a series. For example, in a horizontal bar pattern, the projector can over time include additional horizontal light bars to the pattern. This change in the pattern can change the width of the light bars, the width between light bars, the position of the light bars on the sample object placed on an object platform 225, or a combination thereof. This alteration of the light pattern can allow the system to more easily detect the depth of the sample object.

Microscope

A microscope 215 can be placed between the light projector 210 and a tunable filter of the system 200. The microscope 215 may be a conventional microscope as known in the art, where the microscope includes an eyepiece lens and an objective lens. The projected light from the light projector 210 can be received through the eyepiece lens of the microscope 215, pass through the body of the microscope 215, and be emitted through the objective lens towards the tissue sample.

Tunable Filter

A tunable filter 220 can be placed between the microscope 215 and the tissue sample. The tunable filter 220 can be tuned to allow the projected light from the microscope 215 to pass through while simultaneously filtering out any surrounding light from reaching the tissue sample. This in turn can increase the accuracy of the system and reduce interfering light from reaching the receiver. Examples of the tunable filter can include, but are not limited to, a liquid crystal tunable filter (LCTF) and tunable bandpass filters.

Receiver

The receiver can include a receiver lens and a charge-coupled device (CCD) 230. The receiver lens 225 can receive light emitted from the tissue sample and passes the light to the CCD 230. The CCD 230 can capture the image emitted from the tissue sample. For example, in fluorescence microscopy, the CCD 230 captures the emitted fluorescence from the tissue sample.

Calibration of the System

Several issues can be mitigated if the system is calibrated prior to operation. For example, under the microscope, the light emanating from the sample can cause the proportion of the lighted area to be larger than the proportion of the dark area, which can be caused by diffusion of the platform surface. While these factors are negligible in macro scenes (e.g. building surfaces) phase matching for micro scenes can be affected. A similar result can occur if the intensity of the projected light is too strong.

Additionally, because the object distance under the microscope is much smaller than that of a larger scene, it can be difficult to ensure that the projector and the camera (e.g., the CCD) are confocal on the surface of the object. With such a small range of depth of field, any minimal height change can make the object not fully visible to the camera. Thus, the depth of field can be measured to ensure that the structured light is within the depth of field range where there is enough resolution to image.

Calibration of the system can be used to determine the relative positional relationship between the projector and the CCD. A calibration pattern can be placed as the sample in the system, such as a checkboard. During calibration, corresponding joints based on the checkboard can be identified and compared to an original joint in order to calculate the value of local homographies. Local homographies can provide an initial calibration of a transformation of a user perspective. An RT transfer matrix (e.g., where R is a rotation matrix and T is a translation matrix) can then be calculated of a viewing angle based on the initial calibration. The RT transfer matrix can allow for the structured light to be used to calculate the depth information of a sample in isolation, which can greatly reduce calculation in the system. For example, a spatial transformation matrix (M), which is based on the RT transfer matrix (e.g., M=K[R|T]), where K is an intrinsic parameter matrix based on distances between focal planes to a view point, can be calculated for the system. The following equation can be built for camera space:

$$\begin{bmatrix} x \\ y \\ z \end{bmatrix} = M \begin{bmatrix} x' \\ y' \\ z' \\ 1 \end{bmatrix}, M = \begin{bmatrix} r_{11} & r_{12} & r_{13} & t_x \\ r_{21} & r_{22} & r_{23} & t_y \\ r_{31} & r_{32} & r_{33} & t_z \end{bmatrix}$$

An intrinsic parameter matrix K can also be used, where:

$$K = \begin{bmatrix} f_x & s & x_0 \\ 0 & f_y & y_0 \\ 0 & 0 & 1 \end{bmatrix}$$

The matrix elements $f_x$ and $f_y$ represent distances between focal planes to the view point. $(x_0, y_0)$ can be the central point of the projector, and s can be a twist parameter.

Further, local homographies can be determined in the system. As discussed above, a calibration pattern can be used for calibrating the system, such as a checkboard. A corner of the checkboard can be represented as $q=[\text{col}, \text{row}, 1]^T$, which is captured by the camera. Thus, the corresponding point on the captured image can be $p=[x, y, 1]^T$. A homography $\hat{H}$ can be determined to satisfy the expression:

$$\hat{H} = \underset{H}{\operatorname{argmin}} \sum_{\forall p} \|q - Hp\|^2$$

As the captured image can be inverted (e.g., due to the system), the corresponding pair [q(n), p(n)] can become [q(n), p(N−n)], and q(n) subsequently can be expressed as q(n)=Hp(N−n). Similarly, the spatial transformation matrix M provides for a captured image that is upside down. M can thus be altered to M' to correct the captured image. An example spatial transformation matrix for the system (M') is displayed below:

$$M' = \begin{bmatrix} -r_{11} & -r_{13} & -r_{12} & t_x \\ r_{21} & r_{23} & r_{22} & t_y \\ r_{31} & r_{33} & r_{32} & t_z \end{bmatrix},$$

where r is a rotational matrix element and t is a transposed matrix element. The system can rely on this matrix and, when detecting images by the CCD, can obtain a two-dimensional distorted image of the structured light. The degree of distortion of the structured light depends on the relative position of the projector and the CCD quality inspection the height of the surface of the object. In some cases, a K-means clustering algorithm can be used to remove background and independent points.

Reconstruction Time Period

The systems described herein allow for the 3-D reconstruction of an object to be performed within a minimal time frame. It should be noted that the calculation time period depends on the frame per second (FPS) limitation of the projection as well as the camera (e.g., CCD). However, even with variable calculation time, the overall time of reconstruction can be minimal. For example, a projector and camera that both have a 30 FPS limitation can provide a completed reconstruction of a sample object in approximately one second.

Exemplary System Setup and Implementation

A schematic of an exemplary microscopy system setup is provided in FIG. 4. The system includes two separated lens sets. One lens set 410 is used for the DLP projector 405 and the other lens set 415 is a receiver CCD 420. The DLP projector 405 includes a digital micromirror device (DMD), which generates the patterns of the structured light. The structured light can include a set of horizontal and vertical black and white lines. The number of lines on each pattern can gradually increase over time, thereby decreasing the distance between the lines and increasing the details or reconstruction of the sample. For example, a dense pattern can include approximately 500 lines on a 1.8 cm×1.1 cm area, which provides a resolution of 0.34 μm per pixel.

A tunable filter 425 can be placed between the projector and the object 430. The tunable filter 425 can decrease the intensity of the projected structured light pattern, thereby mitigating possible errors in calibrating the CCD 420 due to saturation. Another example of an exemplary microscopy system is provided in FIG. 3.

The two lens sets 410 and 415 can be initially focused on the same platform to provide a clear image of the object and structured light. The focal point of the system can then be adjusted and the calibration object of a checkboard (e.g., where the checkboard has a lattice length of 0.7 mm) can then be used to perform the system calibration. In some cases, the calibration object can be included within a shroud of CCD 420. In these cases, the calibration process can be performed quickly without requiring repositioning the CCD 420

Figure 5:
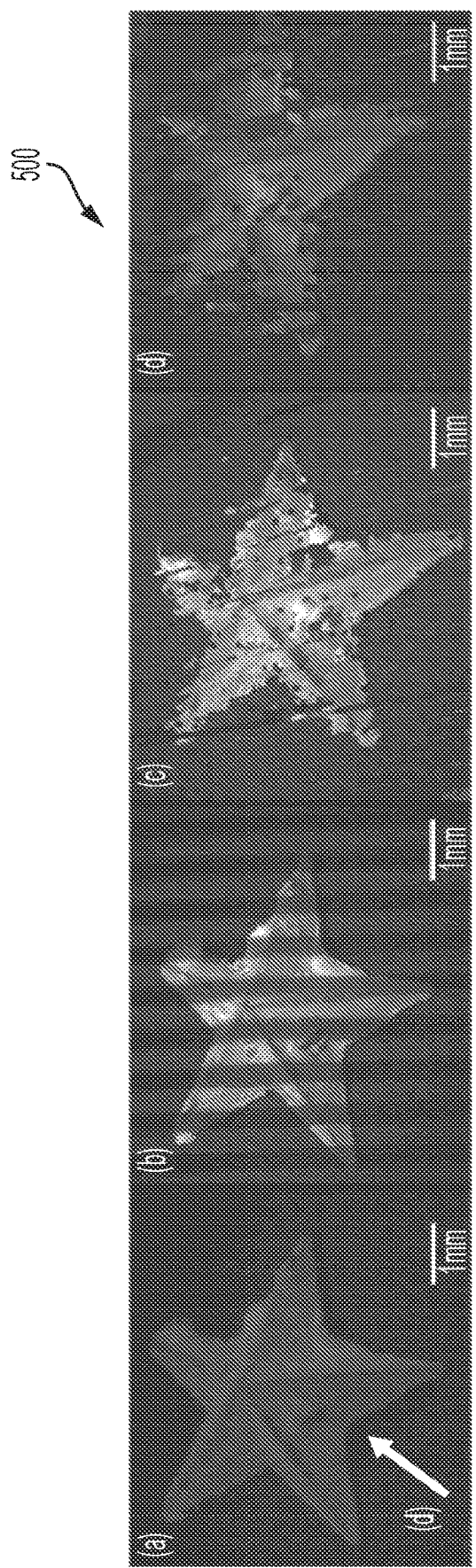
FIG. 5 depicts an image process for a subject according to an embodiment of the invention.

FIG. 1 illustrates an object 100 used as the sample in the system, as well as different stages of reconstructing the object using the system. Image (a) of FIG. 1 provides for a photograph of a 3-D printed star used as the sample in the system. The star has a length of 7 mm and a height of 2.5 mm. Image (b) provides a photograph of the 3-D printed star with structured light emitted onto the star. Image (c) depicts a reconstruction point cloud of the star using the system. Image (d) provides a heat map of the star. The heatmap visualizes the depth information with different colors after optimization. The depth of the star point cloud is between 0 to 2.5 mm approximately, which approximately mirrors the depth of the original 3-D printed star. FIG. 5 provides for a set of images 500 of the original 3-D star, the 3-D star with patterned light, and reconstructed images of the 3-D star.

Exemplary Process Flows

Figure 6:
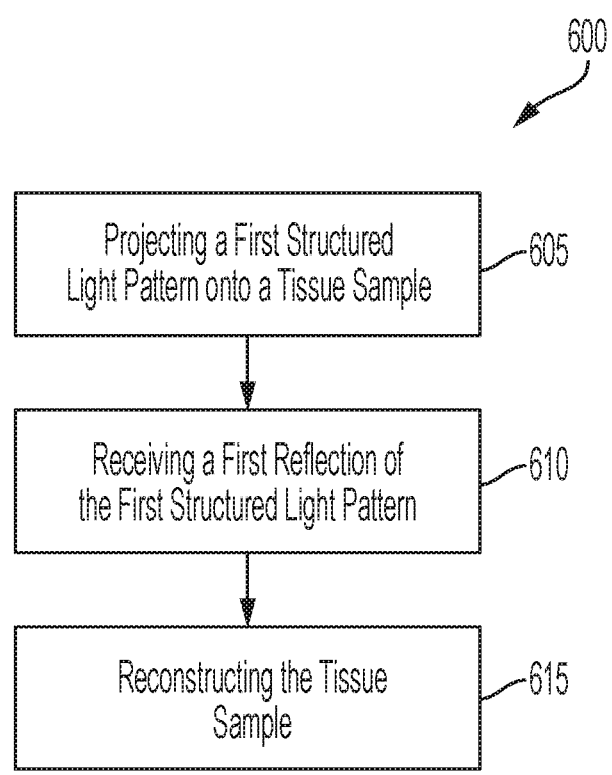
FIGS. 6 and 7 depict processes for noninvasive 3-D fluorescence microscopy according to embodiments of the invention.

An exemplary method of digitally reconstructing a patient tissue sample is depicted in the context of FIG. 6. The method can be implemented by a system, such as systems 200, 300, or 400, as described with reference to FIGS. 2, 3, and 4, respectively.

In Step 605, a first structured light pattern is projected onto the patient tissue sample. The first structured light pattern can be a predetermined light pattern, such as a barred (e.g., horizontal bars, etc.) pattern, or a latticed pattern, that allows for portions of the patient tissue sample to be highlighted and for other areas of the patient tissue sample to not receive projected light. Further, the light can be a single wavelength of light, or can be multiple wavelengths.

For example, a user (e.g., a medical professional such as a doctor, nurse, and the like) can position an imager over a tissue (e.g., skin) surface. In some embodiments, the imager includes a shroud to isolate the imager from ambient radiation (e.g., visible light). The imager may include a viewing window and/or a digital screen to allow the user to visually position the imager before applying the structured light pattern. The tissue can include an object of potential interest such as an actual or potential skin pathology, skin lesion, melanoma, and the like.

In Step 610, a first reflection of the first structured light pattern is received from the patient tissue sample. The first reflection can be fluorescence used in fluorescence microscopy. For example, the patient tissue sample can absorb the first structured light pattern and emit the first reflection, where the first reflection light can have a varied wavelength based on the composition of a portion of the patient tissue sample that absorbs the first structured light pattern.

In Step 615, the patient tissue sample is reconstructed based on the first reflection and the projected first structured light pattern. The patient tissue sample can be reconstructed based on the original light pattern projected compared to the received light pattern reflected from the patient tissue sample. Further, reconstruction can account for possible light intensity issues, focus issues, pattern deformation issues, or a combination thereof, based on a calibration process.

Figure 7:
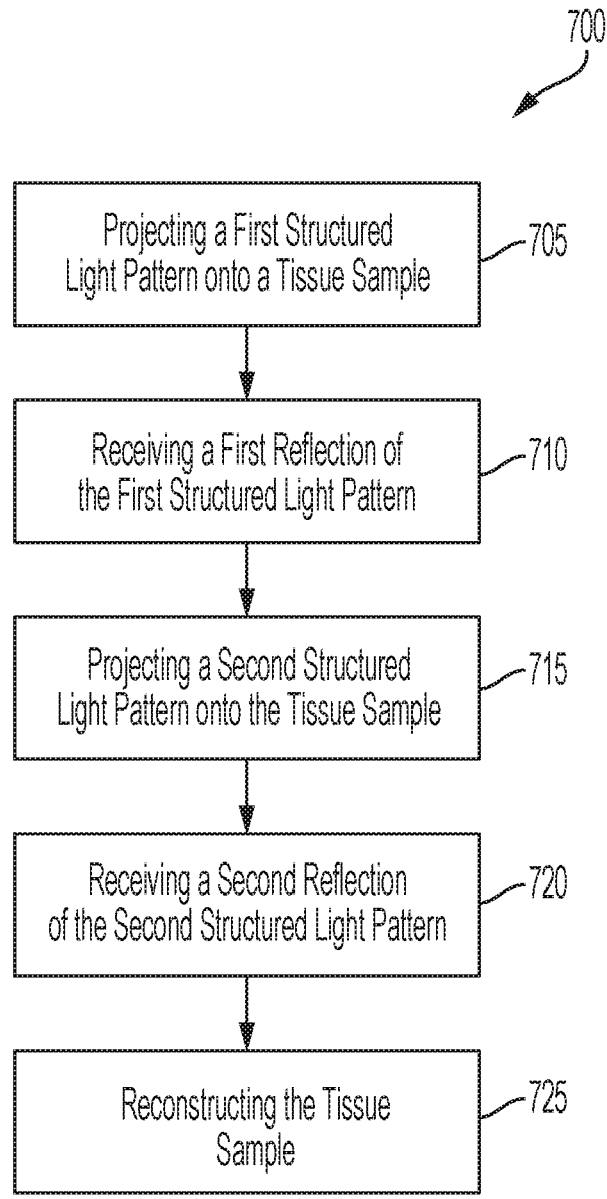

Another exemplary method of digitally reconstructing a patient tissue sample is depicted in the context of FIG. 7. The method can be implemented by a system, such as systems 200, 300, or 400, as described with reference to FIGS. 2, 3, and 4, respectively.

In Step 705, a first structured light pattern is projected onto the patient tissue sample. The first structured light pattern can be a predetermined light pattern, such as a barred (e.g., horizontal bars, etc.) pattern, or a latticed pattern, that allows for portions of the patient tissue sample to be highlighted and for other areas of the patient tissue sample to not receive projected light. Further, the light can be a single wavelength of light, or can be multiple wavelengths.

In Step 710, a first reflection of the first structured light pattern is received from the patient tissue sample. The first reflection can be fluorescence used in fluorescence microscopy. For example, the patient tissue sample can absorb the first structured light pattern and emit the first reflection, where the first reflection light can have a varied wavelength based on the composition of a portion of the patient tissue sample that absorbs the first structured light pattern.

In Step 715, a second structured light pattern is projected onto the patient tissue sample. The second structured light pattern can be different than the first structured light pattern. For example, the second structured light pattern can include an additional horizontal light bar compared to the first structured light pattern, which can decrease the width between the horizontal light bars in the pattern.

In Step 720, a second reflection of the second structured light pattern is received from the patient tissue sample. The second reflection can be fluorescence used in fluorescence microscopy, similar to the first reflection of Step 710.

In Step 725, the patient tissue sample is reconstructed based on the first reflection, the second reflection, the projected first structured light pattern, and the projected second structured light pattern. The patient tissue sample can be reconstructed based on the original first light pattern projected compared to the received first light pattern reflected from the patient tissue sample. The reconstruction can also be based on the original second light pattern projected compared to the received second light pattern reflected from the patient tissue sample. Additionally, the first comparison and the second comparison can also be contrasted, or the first comparison can be contrasted with the first reflection or the first structured light pattern, etc. Further, reconstruction can account for possible light intensity issues, focus issues, pattern deformation issues, or a combination thereof, based on a calibration process.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method for digitally reconstructing a patient tissue sample, the method comprising:
   projecting a first structured light pattern onto the patient tissue sample, the patient tissue sample being on a live human body;
   receiving a first reflection of the first structured light pattern from the patient tissue sample;
   comparing the first reflection and the first structured light pattern;
   determining a depth of a portion of the patient tissue sample based on the comparing; and
   reconstructing the patient tissue sample based on the first reflection and the projected first structured light pattern,
   wherein the first light pattern is projected onto the patient tissue sample for less than 5 ms.

2. The method of claim 1, further comprising:
   projecting a second structured light pattern onto the patient tissue sample subsequent to the projected first structured light pattern;
   receiving a second reflection of the second reflection of the second structured light pattern from the patient tissue sample; and wherein reconstructing the patient tissue sample is further based on the second reflection and the projected second structured light pattern.

3. The method of claim 2, wherein the projected second structured light pattern is projected onto the patient tissue sample at a predetermined angle relative to the projected first structured light pattern, wherein reconstructing the patient tissue sample is further based on the predetermined angle.

4. The method of claim 1, wherein the patient tissue sample comprises an uncut and untreated tissue sample.

5. The method of claim 1, wherein a surface area for the patient tissue sample is less than 1 cm$^2$.

6. The method of claim 1, wherein the projected first structured light pattern comprises a set of horizontal lines, a set of vertical lines, or a combination thereof.

7. The method of claim 6, wherein a spacing between two adjacent vertical lines or two adjacent horizontal lines comprises 0.05 mm.

8. The method of claim 1, further comprising:
displaying the reconstructed patient tissue sample on a graphical user interface.

9. A system for digitally reconstructing the patient tissue sample according to the method of claim 1, comprising:
a projector adapted or configured to project the first structured light onto the patient tissue sample;
a charge-coupled device (CCD) adapted or configured to receive the first reflection from the patient tissue sample; and
a reconstruction device adapted or configured to reconstruct the patient tissue sample based on the first reflection and the projected first structured light pattern.

10. The system of claim 9, further comprising:
a tunable filter positioned between the projector and the patient tissue sample, the tunable filter adapted or configured to reduce a surrounding light intensity being received by the patient tissue sample.

* * * * *